United States Patent
Chakraborty et al.

(10) Patent No.: US 7,945,390 B2
(45) Date of Patent: May 17, 2011

(54) SYSTEM AND METHOD FOR MILD COGNITIVE IMPAIRMENT CLASS DISCOVERY USING GENE EXPRESSION DATA

(75) Inventors: Amit Chakraborty, Cranbury, NJ (US); Dorin Comaniciu, Princeton Jct., NJ (US); Lu-yong Wang, Plainsboro, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1107 days.

(21) Appl. No.: 11/249,004

(22) Filed: Oct. 12, 2005

(65) Prior Publication Data

US 2006/0094044 A1 May 4, 2006

Related U.S. Application Data

(60) Provisional application No. 60/619,798, filed on Oct. 18, 2004.

(51) Int. Cl.
*G01N 33/50* (2006.01)
(52) U.S. Cl. ............. 702/19; 600/300; 702/20; 128/920
(58) Field of Classification Search .................. None
See application file for complete search history.

(56) References Cited

OTHER PUBLICATIONS

Ho et al. (Neuroscience Letters, vol. 298, p. 191-194, 2001).*
Dettling et al. (Bioinformatics, vol. 19, No. 9, p. 1061-1069, 2003).*
Kearns et al. (Journal of Computer and System Sciences, vol. 58, p. 109-128, 1999).*
Friedman et al. (The Annals of Statistics, vol. 28, No. 2, 337-407, 2000).*
Pujol et al. (FIMH 2003, LNCS 2674, p. 242-251, 2003).*
DeLeon et al. (PNAS, vol. 98, No. 19, p. 10966-10971, Sep. 11, 2001).*
Pierce et al. (Neurochemical Research, vol. 29, No. 6, pp. 1145-1152, Jun. 2004).*
Eibl et al. (ECML, LNAI 2430, pp. 72-83, 2002).*
Voisin et al. (Current Opinion in Neurology, vol. 16, p. s43-s45, 2003 ).*
Petersen et al. (Archives of Neurology, vol. 58, No. 12, p. 1985-1992, 2001).*
Günter et al. (MCS 2003, LNCS 2709, pp. 326-335, 2003).*

* cited by examiner

*Primary Examiner* — Karlheinz R Skowronek

(57) ABSTRACT

A system and method for mild cognitive impairment (MCI) class discovery using gene expression data are provided. The method comprises: acquiring gene expression data of a patient having MCI; and identifying a putative MCI subtype based on an expression signature in the gene expression data, wherein the putative MCI subtype is identified by using a boosting tree.

14 Claims, 5 Drawing Sheets

US 7,945,390 B2

SYSTEM AND METHOD FOR MILD COGNITIVE IMPAIRMENT CLASS DISCOVERY USING GENE EXPRESSION DATA

CROSS-REFERENCE TO RELATED APPLICATION

This application claims the benefit of U.S. Provisional Application No. 60/619,798, filed Oct. 18, 2004, the disclosure of which is herein incorporated by reference.

BACKGROUND OF THE INVENTION

1. Technical Field

The present invention relates to class discovery, and more particularly, to a system and method for mild cognitive impairment class discovery using gene expression data.

2. Discussion of the Related Art

Alzheimer's disease (AD) is a progressive neurodegenerative disorder and is one of the most common causes of dementia in the elderly and is one of the leading causes of death in developed countries. AD is clinically characterized by progressive intellectual deterioration together with declining activities of daily living and neuropsychiatric symptoms or behavioral changes.

An early symptom of AD is memory loss, which usually manifests itself as minor forgetfulness that increases with the progression of the disorder. As the disorder progresses, cognitive impairment extends to the domains of language (e.g., aphasia), coordinated movement (e.g., apraxia) and recognition (e.g, agnosia) and to functions such as decision-making and planning that are closely related to the frontal lobe of the brain.

If an effort to find a cure for AD, the molecular mechanism of AD has drawn much attention, but its pathogenesis is still largely undetermined. For example, it is still uncertain as to whether the central mechanism of AD neuro-degeneration is β-amyloid or neurofibrillary tangles (NFT) of tau protein. Recently, mild cognitive impairment (MCI), which is a syndrome of memory impairment that does not significantly affect daily activities and is not accompanied by declines in overall cognitive function, has been identified as a potential transitional stage between normal aging and dementia.

For example, research has found that between 6 to 25 percent of people with MCI progress to AD. Further, many experts have posited that MCI as well as typical age-related memory loss is an early form of AD and thus progression to symptomatic AD would eventually occur. Thus, MCI is becoming increasingly recognized as a risk factor for AD.

Global genomic mapping of the brain and medical imaging of the brain have been used to understand the structure and function of a variety of diseases. This analysis has also been used on AD patients to gain further insight into gene expression in healthy and diseased brains.

Although gene expression analysis has shown promise in identifying an d aiding in the treatment of AD, it has not been used to definitively identify what causes the onset of AD. Accordingly, there is a need for a technique of using gene expression data to identify the onset of AD for aiding in the diagnosis and treatment of AD.

SUMMARY OF THE INVENTION

The present invention overcomes the foregoing and other problems encountered in the known teachings by providing a system and method for MCI class discovery using gene expression data.

In one embodiment of the present invention, a method for MCI class discovery using gene expression data, comprises: acquiring gene expression data of a patient having MCI; and identifying a putative MCI subtype based on an expression signature in the gene expression data, wherein the putative MCI subtype is identified by using a boosting tree.

The gene expression data is acquired from a DNA microarray.

Identifying a putative MCI subtype based on an expression signature in the gene expression data comprises: determining an empirical distribution of the gene expression data; and training a strong classifier using a boosting algorithm to construct the boosting tree, wherein the boosting tree identifies the putative MCI subtype.

Training a strong classifier using a boosting algorithm comprises: determining if an error rate of the strong classifier is less than an error rate threshold, wherein if the error rate is less than the error rate threshold, the boosting tree is used to identify the putative MCI subtype; determining a depth of the boosting tree, wherein if the depth of the boosting tree is greater than a maximum depth threshold, construction of the boosting tree stops and the putative MCI subtype is identified, wherein if the depth of the tree is less than the maximum depth threshold, first and second sets are initialized; and determining first and second probabilities for the gene expression data using the strong classifier, wherein if the first probability and the second probability are greater than the error rate threshold, the weight of the gene expression data is normalized.

The boosting algorithm is one of AdaBoost or RankBoost.

The method further comprises: acquiring first image data of the patient having MCI using a positron emission tomography (PET) technique; acquiring second image data of the patient having MCI using a magnetic resonance imaging (MRI) technique; and receiving cerebrospinal fluid (CSF) specimen data from the patient.

The method further comprises determining whether the putative MCI subtype correlates with AD by using the first and second image data and the CSF specimen data. The method further comprises: assigning the putative MCI subtype to an MCI class.

In another embodiment of the present invention, a system for MCI class discovery using gene expression data, comprises: a memory device for storing a program; a processor in communication with the memory device, the processor operative with the program to: acquire gene expression data of a patient having MCI; and identify a putative MCI subtype based on an expression signature in the gene expression data, wherein the putative MCI subtype is identified by using a boosting tree.

The gene expression data is acquired from a DNA microarray.

The processor is further operative with the program code when identifying a putative MCI subtype based on an expression signature in the gene expression data to: determine an empirical distribution of the gene expression data; and train a strong classifier using a boosting algorithm to construct the boosting tree, wherein the boosting tree identifies the putative MCI subtype.

The processor is further operative with the program code when training a strong classifier using a boosting algorithm to: determine if an error rate of the strong classifier is less than an error rate threshold, wherein if the error rate is less than the error rate threshold the boosting tree is used to identify the putative MCI subtype; determine a depth of the boosting tree, wherein if the depth of the boosting tree is greater than a maximum depth threshold, construction of the boosting tree stops and the putative MCI subtype is identified, wherein if the depth of the tree is less than the maximum depth threshold, first and second sets are initialized; and determine first and second probabilities for the gene expression data using the strong classifier, wherein if the first probability and the second probability are greater than the error rate threshold, the weight of the gene expression data is normalized.

The boosting algorithm is one of AdaBoost or RankBoost.

The processor is further operative with the program code to: acquire first image data of the patient having MCI using a PET device; acquire second image data of the patient having MCI using an MRI device; and receive CSF specimen data from the patient.

The processor is further operative with the program code to determine whether the putative MCI subtype correlates with AD by using the first and second image data and the CSF specimen data. The processor is further operative with the program code to assign the putative MCI subtype to an MCI class.

In yet another embodiment of the present invention, a method for MCI class discovery using gene expression data of a patient having or suspect of having MCI, comprises: acquiring gene expression data of the patient; identifying a putative MCI subtype based on an expression signature in the gene expression data, wherein the putative MCI subtype is identified by constructing a boosting tree, wherein the boosting tree trains a strong classifier using an AdaBoost boosting algorithm to construct the boosting tree to identify the putative MCI subtype; and assigning the putative MCI subtype to an MCI class.

The method further comprises: acquiring first image data of the patient having MCI using a PET technique; acquiring second image data of the patient having MCI using an MRI technique; and obtaining CSF specimen data from the patient, wherein the first and second image data and CSF specimen data are obtained over time.

The method further comprises: determining whether the putative MCI subtype correlates with AD by using the first and second image data and the CSF specimen data obtained over time. The boosting tree operates in a top-down fashion.

The foregoing features are of representative embodiments and are presented to assist in understanding the invention. It should be understood that they are not intended to be considered limitations on the invention as defined by the claims, or limitations on equivalents to the claims. Therefore, this summary of features should not be considered dispositive in determining equivalents. Additional features of the invention will become apparent in the following description, from the drawings and from the claims.

DETAILED DESCRIPTION OF EXEMPLARY EMBODIMENTS

Before discussing the exemplary embodiments of the present invention, a brief description of the proposed molecular mechanism of AD will be discussed followed by a brief overview of MCI and its subtypes.

Figure 1:
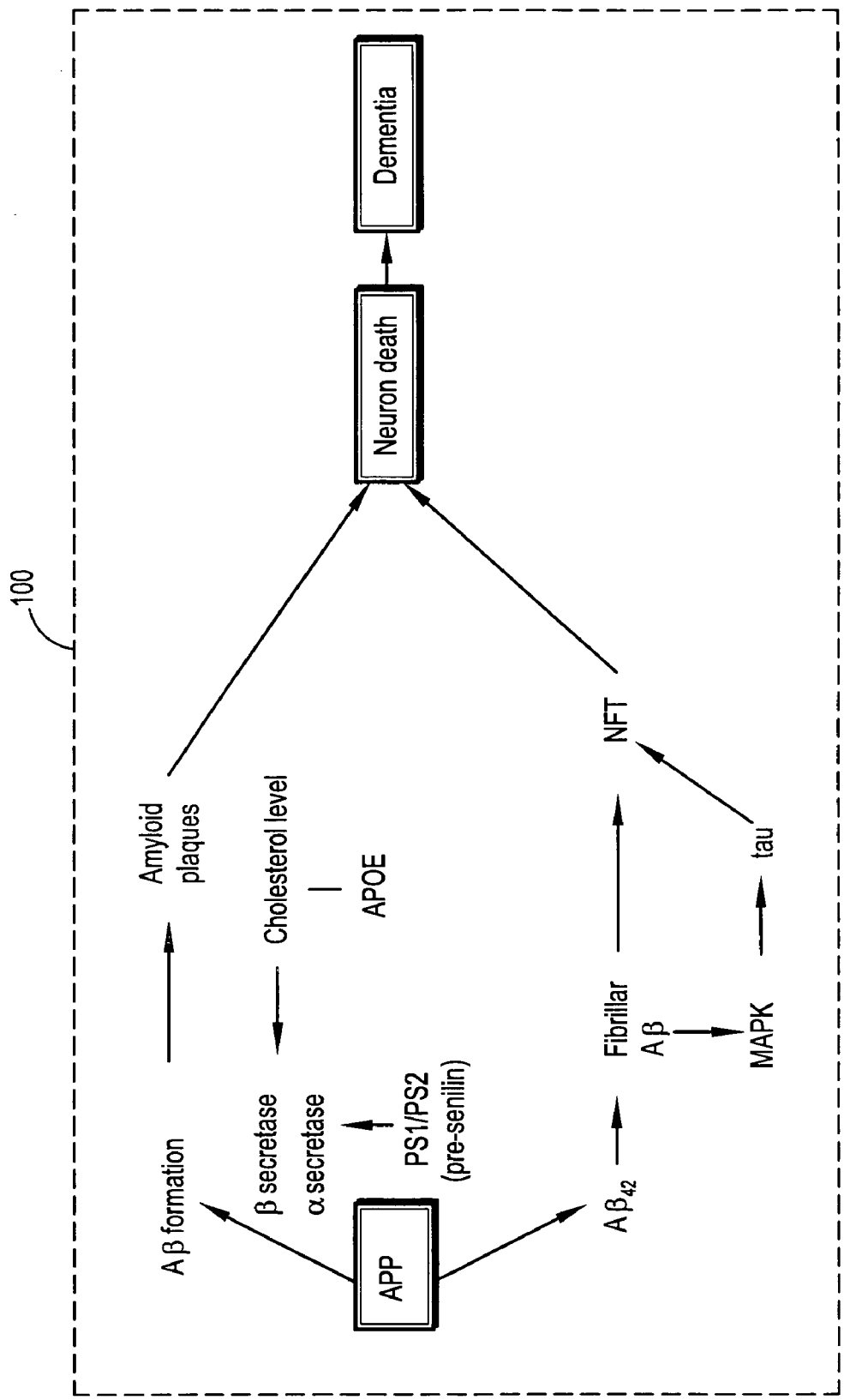
FIG. 1 is a diagram of a proposed molecular mechanism of AD.

As shown by a diagram 100 of the proposed molecular mechanism of AD in FIG. 1, a vital event leading to AD (e.g., dementia) appears to be the formation of amyloid betas (Aβs). Amyloid betas cluster into amyloid plaques (e.g., senile plaques) on exterior surfaces of neurons and thereby lead to neuron death. An Aβ peptide is formed by an amyloid precursor protein (APP). There are two types of Aβ peptides: the 42 amino-acid amyloid beta peptide $A\beta_{42}$ and the 40 amino acid amyloid beta peptide $A\beta_{40}$. Fibrils of $A\beta_{42}$ have been shown to bundle together to form amyloid plaques.

Following amyloid plaque formation, two processes: inflammation and NFTs are believed to play a significant role in causing the death of a neuron. With regard to inflammation, two types of brain cells are involved in the immune/inflammatory response, they are: astrocytes and microglial. Astrocytes increase with the onset of AD and are activated to generate prostaglandin/arachidonic acid mediated inflammation. Activated microglial create damaging free radicals. The activities of astrocytes and microglial have been shown to lead to the death of neurons.

The tau protein (τ) is an essential protein that maintains the structural integrity of microtubules. In AD, however, the tau protein is hyper-phosphorylated and loses the capacity to bind to microtubules. The hyper-phosphorylated tau proteins bind to each other, wrapping themselves into knots with two threads of tau protein being wound around each other such as, for example, NFTs. Neurons full of NFTs rather than functional microtubules soon die. There is evidence that β-amyloid fibrils form pores in neurons leading to calcium influx and the neuron death associated with AD.

It is still undetermined whether the central mechanism of AD neurodegetation is β-amyloid or NFTs of tau protein. For example, it may be that the formation of amyloid plaques is an early event and that the formation of NFTs is a late event. The underlying processes of AD make each event seemly independent. Based on previous experiments, amyloid plaques which were applied to cultured neurons and injected into the brains of non-human primates both lead to NFTs. Further, fibrillar Aβ can induce mitogen-activated protein kinase (MAPK) to lead to tau phosphorylation and thus NFTs.

For example, MAPK pathways abnormally increase in AD, while they usually decrease with the aging of immune system. Amyloid beta is always a feature of AD, but NFT is not. However, amyloid is not essential to cause the cell death of AD, instead tau has been shown to be essential for AD degeneration. Amyloid plaques typically appear first in the association areas of the cerebral cortex, whereas NFTs usually begin in the entohinal cortex. NFTs develop most frequently in large pyramidal neurons with long cortical-cortical connections. NFTs are associated with the origin of corticocortical projections whereas amyloid plaques are associated with the termination of corticocortical projections.

The neurons being killed in the greatest numbers by NFTs are: (1) large pyramidal neurons in the entorhinal cortex, which forward inputs from association cortices to the hippocampus via the perforant path; (2) large cholinergic (acetylcholine-transmitting) neurons in the basal nucleus of Meynart; and (3) output neurons in the CA1 region of the hippocampus. All three classes are output neurons.

As previously discussed, MCI is an intermediate zone between normal cognition and dementia. Clinicians tend to view MCI differently. For example, MCI is seen either as a disease representative of a homogeneous population of individuals in an early prodromal stage of clinically defined AD or a heterogeneous syndrome representing an early or transitional stage of different forms of dementia.

Table 1 illustrates several subtypes of MCI that are believed to represent prodromal stages for several dementing illnesses.

TABLE I

| Type of MCI | May progress to: |
| --- | --- |
| Amnestic | AD |
| Multiple domains, mild impairment | AD |
|  | Vascular dementia |
|  | Dementia with Lewy bodies |
|  | Normal aging |
| Single non-memory domain | Frontotemporal dementia |
|  | Primary progressive aphasia |
|  | Dementia with Lewy bodies |
|  | Vascular dementia |

As shown in Table 1, MCI can affect a single cognitive memory or non-memory domain. In amnestic MCI, memory is affected to a significant degree (e.g., approximately 1.5 SD below age- and education-matched normal subjects), while other domains might be mildly impaired at perhaps less than 0.5 SD below appropriate comparison subjects. In multiple domain MCI, several cognitive domains are impaired at perhaps the 0.5-1.0 SD level of impairment. Single non-memory domain MCI is characterized by a person having a relatively isolated impairment in a single non-memory domain such as executive function, visuospatial processing or language.

A system for MCI class discovery using gene expression data according to an exemplary embodiment of the present invention will now be described with reference to FIG. 2.

Figure 2:
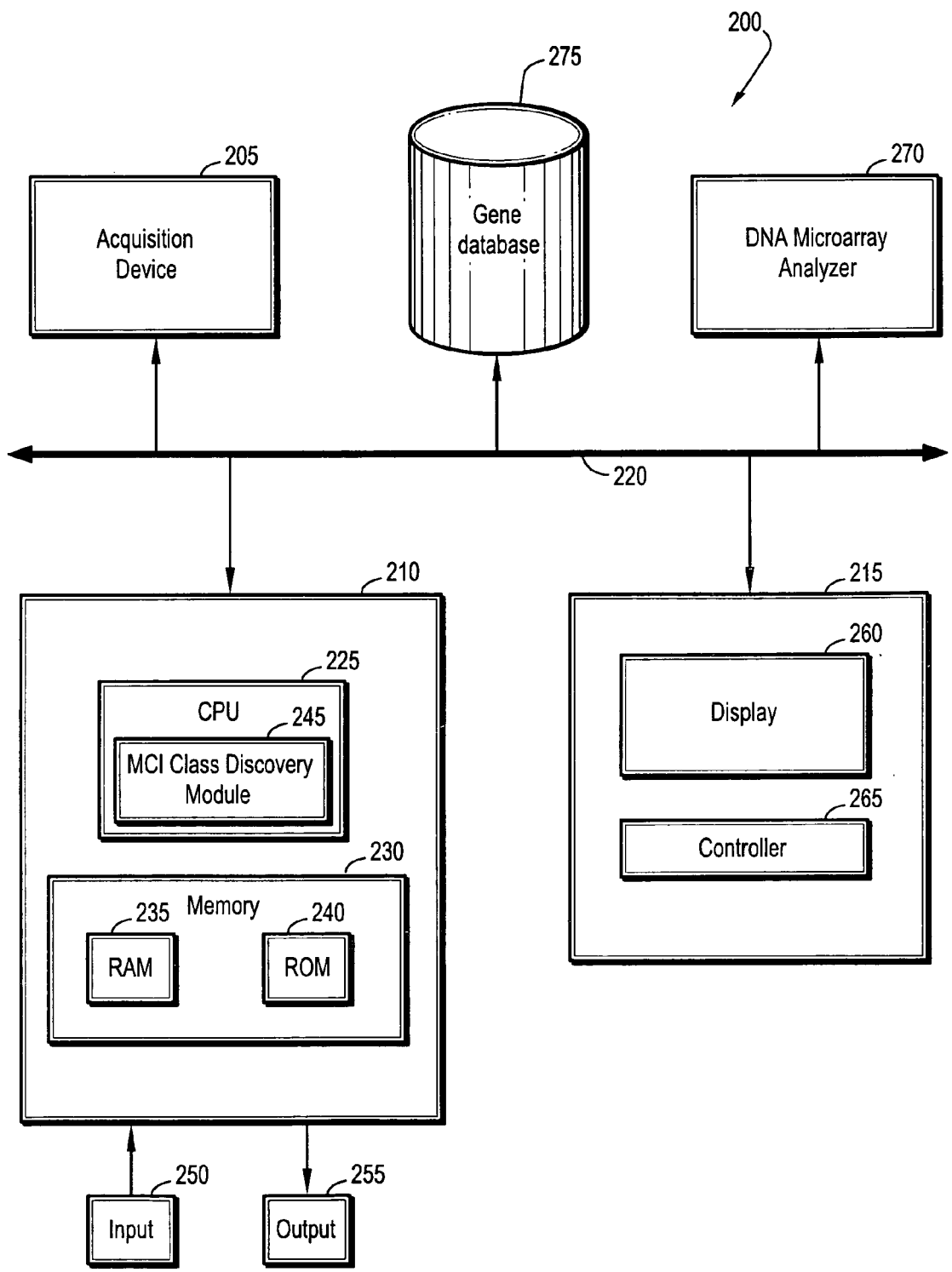
FIG. 2 is a block diagram of a system for MCI class discovery using gene expression data according to an exemplary embodiment of the present invention.

As shown in FIG. 2, the system 200 includes, inter alia, an acquisition device 205, a personal computer (PC) 210, an operator's console 215, a DNA microarray analyzer 270 and a gene database 275 connected over, for example, an Ethernet network 220.

The acquisition device 205 may be a magnetic resonance imaging (MRI) device, a computed tomography (CT) imaging device, a helical CT device, a positron emission tomography (PET) device, a two-dimensional (2D) or three-dimensional (3D) fluoroscopic imaging device, a 2D, 3D, or four-dimensional (4D) ultrasound imaging device, or an x-ray device. The acquisition device 205 may also be a hybrid-imaging device capable of CT, MR, PET or other imaging techniques.

The PC 210, which may be a portable or laptop computer or a personal digital assistant (PDA), includes a CPU 225 and a memory 230, which are connected to an input device 250 and an output device 255. The CPU 225 includes an MCI class discovery module 245 that includes one or more methods for MCI class discovery using gene expression data.

The memory 230 includes a random access memory (RAM) 235 and a read only memory (ROM) 240. The memory 230 can also include a database, disk drive, tape drive or a combination thereof. The RAM 235 functions as a data memory that stores data used during execution of a program in the CPU 225 and is used as a work area. The ROM 240 functions as a program memory for storing a program executed in the CPU 225. The input device 250 is constituted by a keyboard or mouse and the output device 255 is constituted by a liquid crystal display (LCD), cathode ray tube (CRT) display or printer.

The DNA microarray analyzer 270 is used to analyze DNA microarrays, which enable the expression levels of large numbers of genes to be simultaneously measured. The DNA microarray analyzer 270 may include a DNA image processing and analysis tool for measuring and visualizing gene expression data.

The gene database 275 is used to store gene expression data. It is to be understood that the gene expression data could be acquired directly from the DNA microarray analyzer 270 or it could be previously acquired gene expression data. For example, the gene database 275 could be a public or private repository of microarray data accompanied by some basic data analysis and/or visualization tools. In addition, the gene database 275 could contain expression data collected by genomics technologies other than microarray such as serial analysis of gene expression (SAGE) and expressed sequence tags (EST) sequencing.

The operation of the system 200 is typically controlled from the operator's console 215, which includes a controller 265 such as a keyboard, and a display 260 such as a CRT display. The operator's console 215 may communicate with the PC 210 or the acquisition device 205 so that 2D image data collected by the acquisition device 205 can be rendered into 3D data by the PC 210 and viewed on the display 260. It is to be understood that the PC 210 can operate and display information provided by the acquisition device 205 absent the operator's console 215, using, for example, the input device 250 and output device 255 to execute certain tasks performed by the controller 265 and display 260.

The operator's console 215 may also communicate with the DNA microarray analyzer 270 to initiate the analysis of DNA microarrays. The operator's console 215 may then cause the results of this analysis to be sent to the gene database 275 for storage or to the PC 210 for further analysis. In addition, the operator's console 215 may be used to access the contents of the gene database 275 so that it may be analyzed using the MCI class discovery module 245 of the PC 210.

The operator's console 215 may also include any suitable a DNA image processing and analysis tool for measuring and visualizing gene expression data. In addition, the operator's console 215 may include an image rendering system/tool/application that can process digital image data of an acquired image dataset (or portion thereof) to generate and display 2D and/or 3D images on the display 260. It is to be understood that the PC 210 may also include a DNA image processing and analysis tool for measuring and visualizing gene expression data from high-density array images and an image rendering system/tool/application for processing digital image data of an acquired image dataset to generate and display 2D and/or 3D images.

A method for MCI class discovery using gene expression data according to an exemplary embodiment of the present invention will now be described.

Since the method for MCI class discovery is based on a learning framework, which utilizes a boosting algorithm as the basic unit for its learning process, a boosting algorithm, AdaBoost, will now be described. It is to be understood, however, that additional boosting algorithms such as Rank-Boost may be used according to an exemplary embodiment of the present invention.

The AdaBoost algorithm first takes input samples, S, where $S=\{(x_1, y_1, w_1) \ldots (x_n, y_n, w_n)\}$ and $x_i \epsilon X$, $y_i \epsilon Y:\{-1, +1\}$. Each $x_i$ belongs to an instance space such as a gene expression profile, $y_i$ belongs to a label set Y $\{+1, -1\}$, and $w_i$ is the weight of the samples S. The weight $w_i$ is typically set to 1 for initialization purposes. The weight $D_t(i)$ of the distribution of the training example i on a round t is then initialized, where $$D_1(i) = \frac{w_i}{\sum w_i},$$

for each $t=1 \ldots T$. In other words, the set of weights of the training examples is initialized.

The AdaBoost algorithm trains a base learner using the distribution $D_t$. This is done by calling a base learning algorithm and repeating it for t rounds. At each iteration, t, the base learner is used to find a weak hypothesis $h_t$: $X \rightarrow \{+1, -1\}$ with an error $\epsilon_t = Pr_{i \sim W_t}[h_t(x_i) \neq y_i]$ appropriate for the distribution. An $$\alpha_t = \frac{1}{2} \ln\left(\frac{1-\varepsilon_t}{\varepsilon_t}\right)$$

is chosen and the weights are then updated, where $$D_{t+1}(i) = \frac{D_t(i) e^{(-\alpha_t y_i h_t(x_i))}}{z_t},$$

with Z being a normalization factor.

It is to be understood that the weights of incorrectly classified examples are usually increased so that the base learner is forced on difficult examples in the training set. The based learner is called again with new weights over the training examples and then the process is iterated. After which, weak hypotheses are combined into a single strong hypothesis using a weighted majority vote, the strong hypothesis being:

$$H(x) = \sum_{t=1}^{T} \alpha_t t_t(x).$$

The discriminative model corresponding to the string classifier, H(x), is $$q(y|x) = \frac{e^{2yH(x)}}{1 + e^{2yH(x)}}.$$

The error rate $\epsilon$ is proven to be bounded by $$\epsilon \leq 2^T \Pi_{t=1}^T \sqrt{\epsilon_t(1-\epsilon_t)}.$$

One of the key features of the AdaBoost algorithm is that misclassified samples of a previous training receive more weights in a subsequent iteration. However, the AdaBoost algorithm does not rule out the chance that correctly classified samples may be misclassified during another iteration. In order to prevent correctly classified samples from being miscalculated during multiple iterations and to discover putative subtypes of MCI in an unsupervised fashion, a probabilistic boosting tree method according to an exemplary embodiment of the present invention will be employed by the method for MCI class discovery using gene expression data.

Figure 3:
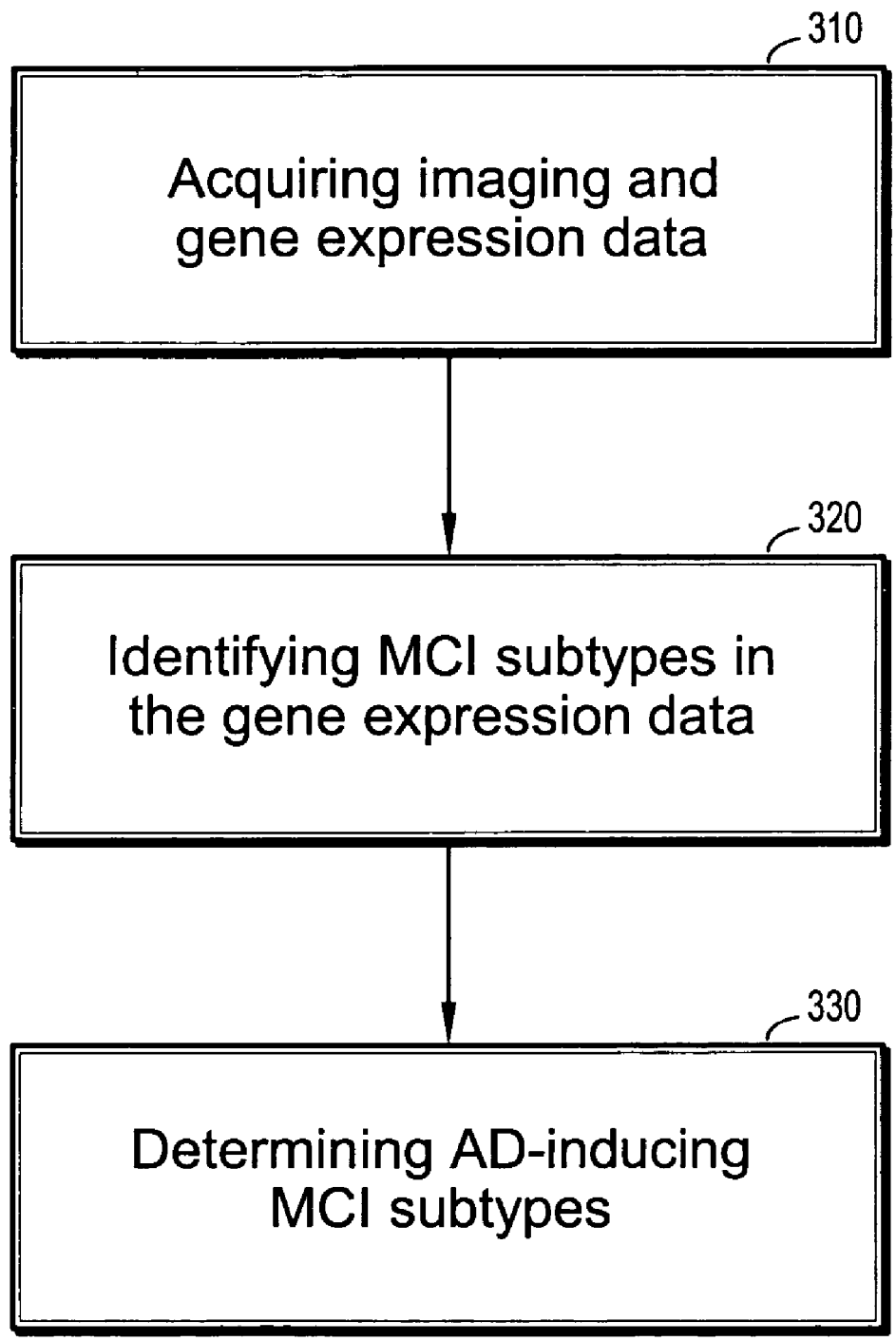
FIG. 3 is a flowchart of a method for MCI class discovery using gene expression data according to an exemplary embodiment of the present invention.

Referring now to FIG. 3, imaging and gene expression data of a patient are acquired (310). The imaging data may be acquired by using the acquisition device 205 in this example a CT scanner, which is operated at the operator's console 215, to scan a patient's head thereby generating a series of 2D image slices associated with the patient's brain. The 2D image slices of the brain are then combined to form a 3D image.

Cerebrospinal fluid (CSF) specimens are obtained from the patients and pathological controls to acquire the gene expression data. A cDNA microarray hybridization is then performed on the CSF specimens to track expression levels of different genes. The resulting gene expression data may then be retrieved using conventional normalization and pre-processing procedures.

Once the imaging and gene expression data have been acquired, MCI subtypes based on expression signatures in the gene expression data are identified (320). This is accomplished by using the probabilistic boosting tree method. Briefly, the probabilistic boosting tree method learns a tree during a training process. For example, at each node of the tree a strong classifier is learned using the AdaBoost algorithm. The training samples are then divided into two sets (e.g., left and right) using the learned classifier and a left sub-tree and right sub-tree are trained. The probabilistic boosting tree method will now be discussed with reference to FIG. 4.

In order to show the probabilistic boosting method in a simplistic format, the probabilities computed by each learned iteration of the AdaBoost algorithm are shown as:

$$q(+1|x) = \frac{e^{2H(x)}}{1+e^{2H(x)}}, q(-1|x) = \frac{e^{-2H(x)}}{1+e^{-2H(x)}}.$$

Figure 4:
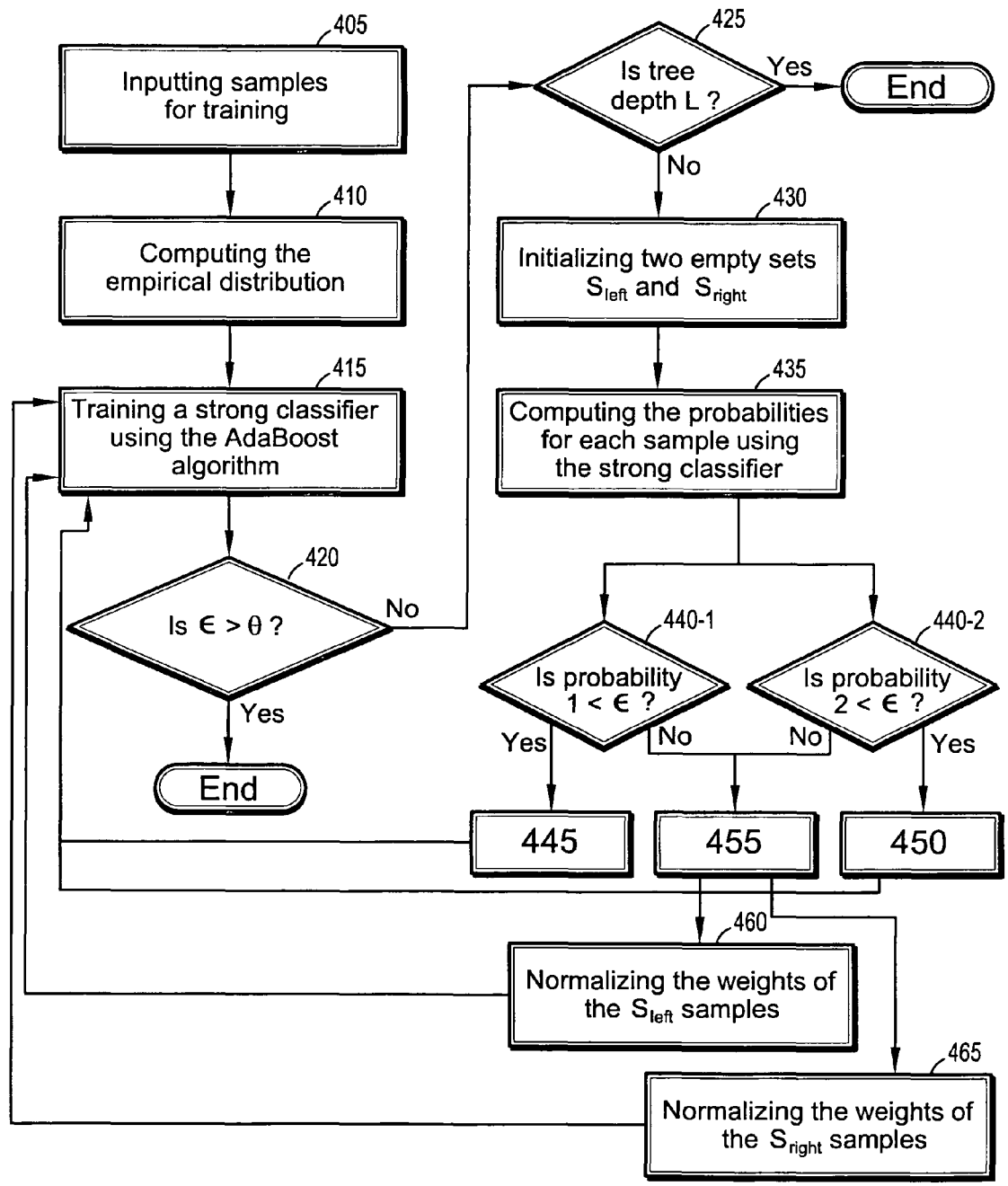
FIG. 4 is a flowchart of a method for identifying MCI subtypes in gene expression data according to an exemplary embodiment of the present invention.

As shown in FIG. 4, similar to that of the AdaBoost algorithm, samples, S, where $S=\{(x_1, y_1, w_1) \ldots (x_n, y_n, w_n)\}$ and $x_i \in X$, $y_i \in Y:\{-1, +1\}$, $\Sigma_i w_i = 1$, are input for training (405). Using the samples, an empirical distribution $\hat{q}(y)$ is computed, where $\hat{q}(y) = \Sigma_i w_i \delta(y_i = y)$ (410). Once the empirical distribution is computed, a strong classifier is trained for the training set S by using the AdaBoost algorithm having a weak classifier T (415).

To control overfitting, a variable $\epsilon$ is used to show support vectors. In other words, the samples should fall in the range of $$\left[\frac{1}{2} - \varepsilon, \frac{1}{2} + \varepsilon\right].$$

The variable $\epsilon$ will also be used in the left and right sub-trees for learning. Thus, if the error rate $\epsilon_t > \theta$, where $\theta$ is a predefined error rate threshold, the AdaBoost algorithm is exited (420). If $\epsilon_t > \theta$ and the current tree depth is greater than a maximum depth threshold, construction of the boosting tree stops, a putative MCI subtype is identified and the AdaBoost algorithm is exited (425). If, however, $\epsilon_t > \theta$ and the current tree depth is less than a maximum depth threshold, two empty sets $S_{left}$ and $S_{right}$ are initialized at the beginning of the tree construction (430). Next, for each sample $(x_i, y_i)$, the probabilities $q(+1|x)$, $q(-1|x)$ are computed using the strong classifier (435).

If the probability $$q(+1|x) - \frac{1}{2} < \varepsilon (440\text{-}1),$$

then $(x_i, y_i, 1) \rightarrow S_{right}$ (445). If the probability $$q(-1|x) - \frac{1}{2} < \varepsilon (440\text{-}2),$$

then $(x_i, y_i, 1) \rightarrow S_{left}$ (450). If the probabilities are not less than the error rate, then $(x_i, y_i, q(+1|x_i)) \rightarrow S_{right}$ and $(x_i, y_i, q(-1|x_i)) \rightarrow S_{left}$ (455). In other words, the training samples are divided into two new sets using learned left and right classifiers which are then used to train a left sub-tree and a right sub-tree.

After step 445, the AdaBoost algorithm is repeated. In other words, the method returns to step 415. After step 450, the AdaBoost algorithm also is repeated by returning to step 415. After step 455, the process may stop once a predefined criteria is met such that the tree branching or deepening is stopped when reaching the maximum tree depth or the weights of the $S_{left}$ samples are normalized (460) and the AdaBoost algorithm is repeated and the weights of the $S_{right}$ samples are normalized (465) and the AdaBoost algorithm is repeated.

As shown in FIG. 4, once the probabilistic boosting tree is trained over the dataset, MCI may be classified and putative subtypes of MCI may discovered. For example, by using the strong classifier determined having an appropriate error rate (e.g., having an error rate is less than θ in step 415), an MCI subtype such as amnestic, multiple domains or single non-memory domains or a putative MCI subtype such as vascular versus neurodegenerative may be identified and then assigned to a known or unknown MCI class. Further, MCI may be discovered by using the AdaBoost classification algorithm to identify gene expression profiles associated with MCI.

For example, since accumulation of AB is thought to be central to the pathogenesis of AD, it is widely accepted that AB may be present in the brain at sublethal concentrations for extended periods before the overt manifestation of AD. Further, neuroimaging with PET provides an excellent tool for in-vivo imaging and quantification of cerebral amyloid load. Thus, referring now back to FIG. 3, by using the above assumption and a PET scan of a patient's brain, AD-inducing MCI subtypes may be determined (330).

For example, by using several PET tracers (e.g., [18F] FDDNP and [11C]PIB), patients having MCI may undergo clinical observation for three years since MCI discovery or onset in order to monitor conversion to clinical dementia. All subjects may receive [11C]PIB, [18F]FDDNP PET scans and a [18F]FDG PET scan during the observation period. Moreover, an MRI scan, a CSF analysis and neuropsychological evaluation for diagnostic purposes may be performed in all subjects. If the patient progresses to clinical dementia, the information provided by the PET tracers in conjunction with MRI analysis and CSF pathological analysis of the patient by a clinician will be used to identify AD-inducing MCI subtypes.

Figure 5:
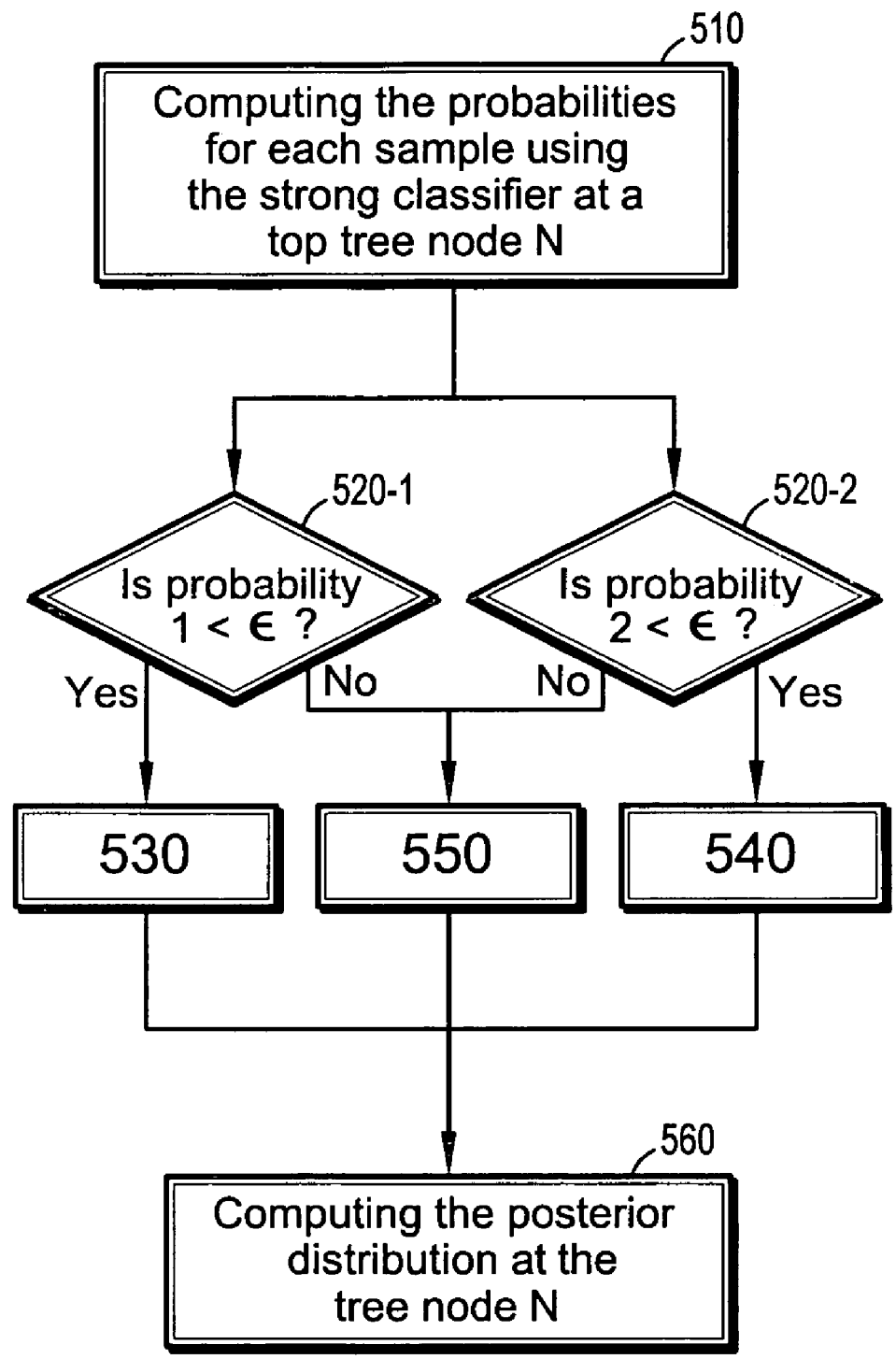
FIG. 5 is a flowchart of a method for identifying MCI subtypes in gene expression data according to another exemplary embodiment of the present invention.

In yet another exemplary embodiment of the present invention, the probabilistic boosting tree method can be performed in a top-down fashion as shown in FIG. 5. In FIG. 5, a posterior distribution $\hat{p}(y|x)$ at a tree node N for a function $F_N(x,y)$ is computed.

As shown in FIG. 5, the process begins from a top node (510). For example, for a sample x, the probabilities $q_N(+1|x)$ and $q_N(-1|x)$ are calculated using the learned AdaBoost model at the tree node N. If $$q_N(+1|x) - \frac{1}{2} < \varepsilon (520\text{-}1),$$

then $\hat{p}_{right}(y) = F_{right(N)}(x, y)$ and $\hat{p}_{left}(y) = \hat{q}_{left(N)}(y)$ where $\hat{q}_{left(N)}(y)$ is the empirical distribution of the left tree (530). If $$q_N(-1|x) - \frac{1}{2} < \varepsilon (520\text{-}2),$$

then $\hat{p}_{right}(y) = q_{right(N)}(x, y)$ and $\hat{p}_{left}(y) = F_{left(N)}(x, y)$ (540). If the probabilities are not less than the error rate (520), then $\hat{p}_{right}(y) = F_{right(N)}(x, y)$ and $\hat{p}_{left}(y) = F_{left(N)}(x, y)$ (550). The resulting posterior distribution at the tree node N is then $\hat{p}_N(y|x) = q(+1|x)\hat{p}_{right}(y) + q(-1|x)\hat{p}_{left}(y)$ (560).

By using this approach, information is gathered during its descent from the top node to report an overall approximated posterior distribution. This approach can also be used to generate a classifier for making hard decisions. For example, as the probabilities q (+1|x) and q (−1|x) are calculated, it can be determined whether to go into the left or right sub-tress by comparing the two probabilities. Referring again to FIG. 5, the prediction of y=+1 (e.g., MCI positive) or y=−1 (e.g., MCI negative) is made at a leaf node of the tree by checking the empirical distribution. The results of this prediction are then passed back to the top node of the tree.

According to an exemplary embodiment of the present invention, an automatic procedure for detecting subtypes of MCI based on gene expression patterns without prior knowledge is provided. This enables an association analysis between putative MCI subtypes and AD to be performed so that the relationship between MCI and AD can be identified. For example, by utilizing genotyping with bioinformatics techniques and phenotyping with medical imaging techniques, the relationship between MCI and AD can be identified thus enhancing the capability for early diagnosis and treatment of AD.

It is to be understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

It is to be further understood that the present invention may be implemented in various forms of hardware, software, firmware, special purpose processors, or a combination thereof. In one embodiment, the present invention may be implemented in software as an application program tangibly embodied on a program storage device (e.g., magnetic floppy disk, RAM, CD ROM, DVD, ROM, and flash memory). The application program may be uploaded to, and executed by, a machine comprising any suitable architecture.

It should also be understood that the above description is only representative of illustrative embodiments. For the convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be straightforwardly implemented without departing from the spirit and scope of the present invention.

It is therefore intended that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A program storage device embodying a program of instructions executable by machine to perform steps for mild cognitive impairment (MCI) class discovery using gene expression data, the steps comprising:
   acquiring gene expression data of a patient having MCI;
   identifying a putative MCI subtype based on an expression signature in the gene expression data, wherein the putative MCI subtype is identified by using a boosting tree training algorithm; and
   outputting the putative MCI subtype to a display,
   wherein the boosting tree training algorithm comprises:
      training a strong classifier on a sample training set with a first boosting algorithm that constructs a boosting tree, in initializing first and second sets based on a depth of the tree, and computing first and second probabilities for each training sample using the strong classifier,
   wherein if the first probability is less than an error of the tree, weighting the first set with one and repeating the boosting algorithm, and if the second probability is less than the error, weighting the second set with one and repeating the boosting algorithm and if the first and second probabilities are not less than the error dividing the samples into first and second classifiers, weighting the samples with a weight equal to the first and second probabilities, respectively, normalizing the weighted samples and repeating the boosting algorithm.

2. The program storage device of claim 1, wherein the gene expression data is acquired from a DNA microarray.

3. The program storage device of claim 1, wherein the first boosting algorithm is one of AdaBoost or RankBoost.

4. The program storage device of claim 1, the steps further comprising:
   acquiring first image data of the patient having MCI using a positron emission tomography (PET) technique;
   acquiring second image data of the patient having MCI using a magnetic resonance imaging (MRI) technique; and
   receiving cerebrospinal fluid (CSF) specimen data from the patient.

5. The program storage device of claim 4, the steps further comprising:
   determining whether the putative MCI subtype correlates with Alzheimer's disease (AD) by using the first and second image data and the CSF specimen data.

6. The program storage device of claim 1, the steps further comprising:
   assigning the putative MCI subtype to an MCI class.

7. The program storage device of claim 1, wherein the boosting tree training algorithm operates in a top-down fashion.

8. The program storage device of claim 1, wherein the putative MCI subtype that is identified by using the boosting tree training algorithm is not identified as another putative MCI subtype in another iteration of the boosting tree training algorithm.

9. A system for mild cognitive impairment (MCI) class discovery using gene expression data, comprising:
   a memory device for storing a program;
   a processor in communication with the memory device, the processor operative with the program to:
   acquire gene expression data of a patient having MCI;
   identify a putative MCI subtype based on an expression signature in the gene expression data, wherein the putative MCI subtype is identified by using a boosting tree training algorithm; and
   output the putative MCI subtype to a display,
   wherein the processor is further operative with the program when executing the boosting tree training algorithm to:
   train a strong classifier on a sample training set with a first boosting algorithm that constructs a boosting tree, end the training if an error of the tree is greater than a first threshold, and if the error is less than the first threshold, determine a depth of the tree, wherein if the tree depth is greater than a second threshold, stop construction of the tree, and if the tree depth is less than the second threshold, initialize first and second sets,
   compute first and second probabilities for each training sample using the strong classifier, wherein if the first probability is less than the error, weight the first set with one and repeat the boosting algorithm, and if the second probability is less than the error, weight the second set with one and repeat the boosting algorithm and if the first and second probabilities are not less than the error divide the samples into first and second classifiers, weight the samples with a weight equal to the first and second probabilities, respectively, normalize the weighted samples and repeat the boosting algorithm.

10. The system of claim 9, wherein the gene expression data is acquired from a DNA microarray.

11. The system of claim 9, wherein the first boosting algorithm is one of AdaBoost or RankBoost.

12. The system of claim 9, wherein the processor is further operative with the program to:
   acquire first image data of the patient having MCI using a positron emission tomography (PET) device;
   acquire second image data of the patient having MCI using a magnetic resonance imaging (MRI) device; and
   receive cerebrospinal fluid (CSF) specimen data from the patient.

13. The system of claim 12, wherein the processor is further operative with the program to:
   determine whether the putative MCI subtype correlates with Alzheimer's disease (AD) by using the first and second image data and the CSF specimen data.

14. The system of claim 13, wherein the processor is further operative with the program to:
   assign the putative MCI subtype to an MCI class.

* * * * *